United States Patent [19]

Burkhard

[11] 4,011,208

[45] Mar. 8, 1977

[54] 3-CYANO OR ACYL-4-ARYL-5-ARYLAZO-6-HYDROXYPYRIDONE-2 DYES

[75] Inventor: Hermann Burkhard, Neu-Allschwil, Switzerland

[73] Assignee: Sandoz Ltd., Basel, Switzerland

[22] Filed: Sept. 11, 1974

[21] Appl. No.: 504,876

Related U.S. Application Data

[63] Continuation-in-part of Ser. No. 148,162, May 28, 1971, abandoned, which is a continuation of Ser. No. 787,585, Dec. 27, 1968, abandoned.

[30] Foreign Application Priority Data

Jan. 18, 1968 Switzerland .................. 787/68

[52] U.S. Cl. .................. 260/156; 260/294.8 R; 260/294.8 E; 260/294.9; 260/295 R; 260/295 AM; 260/297 Z

[51] Int. Cl.² .................. C09B 29/36; D06P 3/26; D06P 3/36; D06P 3/54

[58] Field of Search .................. 260/156

[56] References Cited

UNITED STATES PATENTS

| | | | |
|---|---|---|---|
| 1,606,209 | 11/1926 | De Montmollin et al. | 260/146 D |
| 2,675,375 | 4/1954 | Marson et al. | 260/154 |
| 2,746,951 | 5/1956 | Taube | 260/154 |
| 2,980,665 | 4/1961 | Langley | 260/154 |
| 3,042,648 | 7/1962 | Lewis | 260/154 X |
| 3,083,195 | 3/1963 | Elslager | 260/154 |
| 3,481,918 | 12/1969 | Straley et al. | 260/154 |
| 3,487,066 | 12/1969 | Ritter et al. | 260/156 |

FOREIGN PATENTS OR APPLICATIONS 606,039  11/1934  Germany .................. 260/156

*Primary Examiner*—Floyd D. Higel
*Attorney, Agent, or Firm*—Gerald D. Sharkin; Richard E. Vila; Melvyn M. Kassenoff

[57] ABSTRACT

Compounds of the formula

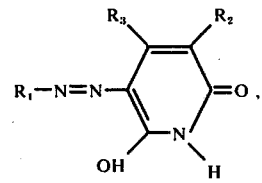

wherein
  $R_1$ is a benzene or naphthalene diazo component,
  $R_2$ is cyano or acyl, and
  $R_3$ is phenyl, naphthyl or heterocyclyl, or a substituted derivative thereof, with the proviso that the molecule is free of sulfo groups, have low solubility in water and are highly suited for dyeing and printing fibers and textiles of synthetic and semi-synthetic, hydrophobic, high molecular weight polymers such as polyesters, cellulose diacetate, cellulose triacetate and polyamides. The obtained dyeings are fast to light, sublimation, thermofixation, pleating, wet treatments, etc. and are stable to permanent press finishing.

15 Claims, No Drawings

3-CYANO OR ACYL-4-ARYL-5-ARYLAZO-6-HYDROXYPYRIDONE-2 DYES

This application is a continuation-in-part of application Ser. No. 148,162, filed on May 28, 1971 and now abandoned, which is a continuation of application Ser. No. 787,585, filed on Dec. 27, 1968 and now abandoned.

The new compounds are of the formula

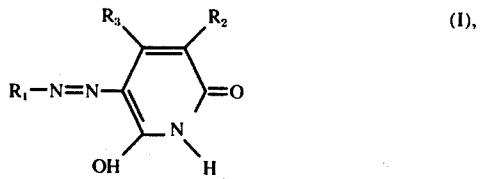

wherein
$R_1$ is a diazo component of the benzene or naphthalene series,
$R_2$ is cyano or acyl, and
$R_3$ is a phenyl, naphthyl or heterocyclic radical which may be substituted, with the proviso that sulfo groups are excluded as possible substituents.

The preferred compounds of this application are those of Formula I
wherein
$R_1$ is phenyl, substituted phenyl, naphthyl or substituted naphthyl (particularly phenyl or substituted phenyl), wherein each substituent of substituted phenyl and substituted naphthyl is independently chloro, bromo, hydroxy, cyano, nitro, trifluoromethyl, alkyl, substituted alkyl, alkoxy, substituted alkoxy, acyl, acyloxy, acylamino, formyl, morpholinosulfonyl, piperidinosulfonyl, morpholinosulfonyloxy, aziridinosulfonyloxy, piperidinosulfonyloxy, alkylsulfamoylanilino, phenylsulfamoylanilino, dinitroanilino, alkylcarbonylaminophenyl, dinitrophenyl, phenylazo, nitrophenylazo, dichlorophenylazo, bromophenylazo, cyanophenylazo, methoxyphenylazo, ethoxyphenylazo, tolylazo or acylphenylazo, wherein each substituent of substituted alkyl and substituted alkoxy is independently chloro, bromo, alkoxy, phenyl, cyano, hydroxy or acyloxy,
$R_2$ is cyano, acyl, thienylcarbonyl or pyridylcarbonyl (particularly cyano or acyl), and
$R_3$ is phenyl, naphthyl, thiazolyl, benzothiazolyl, thienyl, pyrrolyl, furyl, pyridyl, imidazolyl or benzimidazolyl, or a substituted derivative thereof (particularly phenyl or substituted phenyl), wherein each substituent is independently chloro, bromo, alkyl, substituted alkyl, alkoxy, substituted alkoxy, hydroxy, trifluoromethyl, cyano, thiocyano, nitro, alkylamino, dialkylamino, acyl, acyloxy or acylamino,
wherein each substituent of substituted alkyl and substituted alkoxy is independently chloro, bromo, alkoxy, phenyl, cyano, hydroxy or acyloxy,
wherein
each acyl and acyl radical of each acyloxy, acylamino and acylphenlazo is independently R—X— or R'—Y—, wherein R is lower alkyl, substituted lower alkyl, cyclohexyl, phenyl or substituted phenyl, wherein each substituent of substituted lower alkyl is independently chloro, bromo, alkoxy, phenyl, cyano, hydroxy or acyloxy, and each substituent of substituted phenyl is independently chloro, bromo, hydroxy, cyano, nitro, trifluoromethyl, alkyl or alkoxy,
X is —CO—, —O—CO— or —SO$_2$—,
R' is hydrogen or R, and
Y is —NR'—CO— or NR'—SO$_2$—, and
each alkyl, alkoxy and alkyl and alkoxy radical of each substituted alkyl, substituted alkoxy, alkylsulfamoylanilino, alkylcarbonylaminophenyl, alkylamino and dialkylamino independently has 1 to 10 carbon atoms.

In the specially preferred dyes of Formula I,
$R_1$ is a phenyl or naphthyl radical which may be substituted by chlorine or bromine atoms, hydroxy, cyano, nitro, trifluoromethyl, alkyl, alkoxy, acyl, acyloxy, acylamino, alkylaminosulfonylphenylamino, phenylaminosulfonylphenylamino, nitrophenylamino (nitroaniline), alkylcarbonylaminophenyl, phenylazo, chlorophenylazo, bromophenylazo, nitrophenylazo, cyanophenylazo, acylphenylazo, methylphenylazo (tolylazo) or methoxyphenylazo groups,
$R_2$ is a cyano or acyl radical, and
$R_3$ is a phenyl, naphthyl, thiazolyl, benzothiazolyl, thienyl, pyrryl, furyl, pyridyl, imidazolyl or benzomidazolyl radical which may be substituted by chlorine or bromine atoms or by alkyl, alkoxy, hydroxy, trifluoromethyl, cyano, thiocyano, nitro, alkylamino, acyl, acyloxy or acylamino groups; all the alkyl and alkoxy groups contain 1 to 10 carbon atoms and may be substituted by chlorine or bromine atoms, alkoxy, phenyl, cyano, hydroxy or acyloxy groups. The acyl radicals are of the formula R—X— or R'—Y—, wherein R is a hydrocarbon radical which may bear any substituents, other than sulphonic acid groups, and/or hetero atoms, in particular an alkyl radical which has 1 to 4 carbon atoms and may be substituted as stated above, or a phenyl radical substituted by chlorine or bromine atoms, hydroxy, cyano, nitro, trifluoromethyl, alkyl or alkoxy groups,
X is —CO—, —O—CO— or —SO$_2$—,
R' is hydrogen or R,
Y is —NR''CO— or NR''—SO$_2$—
R'' is hydrogen or R.

Also of special interest are the compounds of formula I wherein $R_1$ is substituted phenyl, wherein each substituent of substituted phenyl is independently chloro, bromo, hydroxy, cyano, nitro, trifluoromethyl, lower alkyl, lower alkoxy, acyl, acyloxy, morpholinosulfonyl, piperidinosulfonyl, morpholinosulfonyloxy, aziridinosulfonyloxy, piperidinosulfonyloxy, benzamido, acetamido, 4-phenylsulfamoylanilino, 2,4-dinitroanilino, 4-acetamidophenyl, 2,4-dinitrophenyl, phenylazo, 4-nitrophenylazo, 2,5-dichlorophenylazo, 3-cyanophenylazo, 4-methoxyphenylazo, 4-ethoxyphenylazo, o-tolylazo, 4-acetylphenylazo or 4-methylsulfonylphenylazo, with the proviso that the phenyl ring of substituted phenyl has 1 to 3 substituents,
$R_2$ is cyano or acyl, and
$R_3$ is phenyl, naphthyl, 2-thiazolyl, 5-thiazolyl, 2-benzothiazolyl, 2-thienyl, 3-pyrrolyl, 2-furyl, 3-pyridyl or 2-benzimidazolyl, or a substituted derivative thereof, wherein each substituent is independently chloro, bromo, lower alkyl, lower alkoxy, hydroxy, cyano, thiocyano, nitro, lower alkylamino, dilower alkylamino, acyl, acyloxy or lower alkylcarbonylamino, with the proviso that each substituted derivative has 1 to 3 substituents, wherein each acyl and acyl radical of each acyloxy is independently R—X— or R'—Y—, wherein R is lower alkyl, monosubstituted lower alkyl, cyclohexyl, phenyl or monosubstituted phenyl, wherein the substituent of monosubstituted lower alkyl is chloro, bromo, lower alkoxy, phenyl, cyano or hydroxy, and the substituent of monosubstituted phenyl is chloro, lower alkyl or lower alkoxy, X is —CO—, —O—CO— or —SO₂—, R' is hydrogen or R, and Y is —NR'—CO— or —NR'—SO₂—.

The most preferred compounds are those wherein $R_1$ is phenyl or substituted phenyl, especially substituted phenyl wherein each substituent is independently chloro, cyano, nitro, lower alkyl, lower alkoxy, acyl, acyloxy, morpholinosulfonyloxy, aziridinosulfonyloxy, phenysulfamoylanilino, dinitroanilino, lower alkylcarbonylaminophenyl, dinitrophenyl, phenylazo, nitrophenylazo, dichlorophenylazo, cyanaophenylazo, methoxyphenylazo, ethoxyphenylazo, tolylazo, acetylphenylazo or methylsulfonylphenylazo, wherein each acyl and acyl radical of acyloxy is independently R—X— or R'—Y—, wherein R is lower alkyl, monosubstituted lower alkyl, phenyl or monosubstituted phenyl, wherein the substituent of monosubstituted lower alkyl is lower alkoxy, cyano or phenyl, and the substituent of monosubstituted phenyl is chloro, lower alkyl or lower alkoxy, X is —SO₂— or —O—CO— (particularly the former), R' is hydrogen, lower alkyl, monosubstituted lower alkyl, cyclohexyl, phenyl or monosubstituted phenyl, wherein the substituent of monosubstituted lower alkyl is hydroxy or lower alkoxy and the substituent of monosubstituted phenyl is lower alkyl, lower alkoxy or chloro, and Y is —NR'—SO₂—, $R_2$ is cyano, and $R_3$ is phenyl.

Of the preceding group, compounds wherein $R_1$ is substituted phenyl, and each substituent of substituted phenyl independently is chloro, nitro, cyano, methyl, methoxy, ethoxycarbonyl, 2-methoxyethoxycarbonyl, methylsulfonyl, methylsulfonyloxy, 2-ethoxyethylsulfonyloxy, 2-cyanoethylsulfonyloxy, benzylsulfonyloxy, phenylsulfonyloxy, 4-chlorophenylsulfonyloxy, p-tolylsulfonyloxy, 3-methoxyphenylsulfonyloxy, 4-methoxyphenylsulfonyloxy, dimethylsulfamoyl, di(2-hydroxyethyl)sulfamoyl, phenylsulfamoyl, propylsulfamoyloxy, dimethylsulfamoyloxy, dibutylsulfamoyloxy, cyclohexylsulfamoyloxy, 2-ethoxyethylsulfamoyloxy, phenylsulfamoyloxy, N-methyl-N-phenylsulfamoyloxy, o-tolylsulfamoyloxy, 4-methoxyphenylsulfamoyloxy, 4-chlorophenylsulfamoyloxy, morpholinosulfonyloxy, aziridinosulfonyloxy, 4-phenylsulfamoylanilino, 2,4-dinitroanilino, 4-acetamidophenyl, 2,5-dichlorophenylazo, 3-cyanophenylazo, 4-methoxyphenylazo, 4-ethoxyphenylazo, o-tolylazo, 4-acetylphenylazo or 4-methylsulfonylphenylazo are exemplified.

The new dyes are produced by diazotizing an amine of the formula

$$R_1-NH_2 \qquad (II)$$

and coupling the resulting diazo compound with a compound of the formula

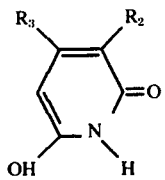

(III)

This compound, or the radical of the coupling component in the compounds of formula I, may be present in tautomeric form:

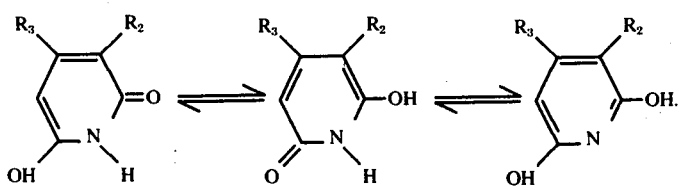

The coupling components of formula III are produced in analogy with the method of J. Guareschi, Att Acc. R.d. Scienze die Torino, 1895/96 (cf. Ber. d. dt. Chem. Ges. 29, 655(1896.) by condensation of appropriately substituted acetic acid amides with suitably substituted β-ketocarboxylic acid esters.

The coupling reaction is generally carried out in acid, if necessary, buffered medium, and with cooling, for example at 3°–9° C.

It is advantageous to convert the dyes of formula I into dye preparations before application, using the known methods, e.g., grinding in the presence of a dispersing agent and/or fillers, followed by drying in a vacuum or atomizer drier. The resulting preparations, after the addition of a suitable amount of water, can be employed for dyeing, padding or printing from long or short baths. From aqueous dispersion the dyes build up excellently on fibers of synthetic and semi-synthetic hydrophobic substances of high molecular weight. The dyes are highly suitable for exhaustion dyeing, pad dyeing and printing of textiles of linear aromatic polyesters, cellulose diacetate, cellulose triacetate and synthetic polyamides. They are also suitable for dyeing polyolefins and polyvinyl compounds.

The known dyeing and printing methods are used, e.g., the process described in French Patent 1,445,371. The dyeings obtained have very good fastness properties, being outstandingly fast to light, sublimation, thermofixation, pleating, ozone, rubbing, alkalis and gas fumes. The wet fastness properties including fastness to water, sea water and washing are also very good. Other notable features are fastness to cross dyeing, reduction stability and good migration. The dyes are stable to the action of various forms of permanent press finishing. Their good power on barry polyester materials is a further advantage. They are suitable for application to texturized polyester fibers.

In the following Examples the parts and percentages are by weight and the temperatures in degrees centigrade.

EXAMPLE 1

A mixture of 17.3 parts of 2-chloro-4-nitroaniline, 100 parts of water and 35 parts of 30% hydrochloric acid is prepared and cooled to 0°. Over 15 minutes a solution of 8 parts of sodium nitrite in 20 parts of water is dropped in and stirring is continued for a further 30 minutes. The excess nitrous acid is then destroyed with amidosulphonic acid. A small amount of a solid impurity is removed by filtration and the clarified diazonium salt solution is added in small portions to a solution of 21.2 parts of 4-phenyl-3-cyano-6-hydroxypyridone-2 in 150 parts of water, adjusted with glacial acetic acid to pH 4.0 – 4.5 and with ice to 0°–5°. During the coupling reaction this pH value is maintained constant with sodium acetate. After completion of the reaction the dye is filtered off, washed until neutral and dried. It is an orange to red powder which dyes synthetic fibers in fast yellow shades.

EXAMPLE 2

16.5 Parts of 4-aminobenzoic acid ethyl ester are mixed with 100 parts of water and 35 parts of 30% hydrochloric acid. The mixture is cooled to 0° and a solution of 8 parts of sodium nitrite in 20 parts of water is dropped into it over 15 minutes, with continued stirring for 30 minutes. The excess nitrous acid is then destroyed with amidosulphonic acid. After filtration to eliminate a small amount of solid impurity, the clear diazonium salt solution is added in small portions at 0°–5° to a solution of 21.2 parts of 4-phenyl-3-cyano-6-hydroxypyridone-2 in 150 parts of water, adjusted to pH 4 with glacial acetic acid. The pH of the coupling solution is maintained at 4.0 – 4.5 with sodium acetate. On completion of the reaction the precipitated dye is filtered off, washed until neutral and dried. It is obtained as yellow to orange crystals, which give dyeings of bright yellow shade on synthetic fibres having excellent fastness properties.

EXAMPLE 3

20 Parts of sulphanilic acid dimethylamide are mixed with 100 parts of water and 35 parts of 30% hydrochloric acid, and the mixture is cooled to 0°. A solution of 8 parts of sodium nitrite in 20 parts of water is added dropwise in 15 minutes and stirring is continued for 45 minutes, after which the excess nitrous acid is decomposed with amidosulphonic acid. For coupling 21.2 parts of 4-phenyl-3-cyano-6-hydroxypyridone-2 are dissolved in 150 parts of water and the solution is adjusted to pH 4.0–4.5 with acetic acid and cooled to 0°–5° with ice. The diazonium salt solution is added in small portions, the pH being kept within the stated values by adding sodium acetate. On completion of the coupling reaction the precipitated dye is filtered off, washed until neutral and dried. It gives yellow dyeings of good fastness on synthetic fibres.

EXAMPLE 4

12.75 Parts of 4-chloroaniline are dissolved in 100 parts of water and 35 parts of 30% hydrochloric acid and the solution is cooled to 0°. A solution of 8 parts of sodium nitrite in 20 parts of water is added dropwise over 15 minutes and stirring continued for 30 minutes, after which the excess nitrous acid is destroyed with amidosulfonic acid. A solution for coupling is prepared with 21.2 parts of 4-phenyl-3-cyano-6-hydroxypyridone-2 in 150 parts of water, adjusted to pH 4.0–4.5 with acetic acid and cooled to 0°–5°. The ice-cold, clarified diazonium salt solution is added to it in small portions, with the addition of sodium acetate to maintain the pH in the stated range. The dye begins to settle out during the addition of the diazonium salt solution. On completion of the reaction it is filtered off, washed until neutral and dried. This dye produces very fast yellow dyeings on synthetic fibres.

When in place of 4-chloroaniline, an equimolar amount of 2,5-dichloroaniline is used, a dye of similar shade with the same good fastness properties is obtained.

Application Examples

A. A mixture of 7 parts of the dye of Example 1, 4 parts of sodium dinaphthylmethane disulphonate, 4 parts of sodium cetyl sulphate and 5 parts of anhydrous sodium sulphate is ground in a ball mill for 48 hours to give a fine powder. One part of the powder is suspended in a little water and the suspension run through sieve into a bath of 400 parts of water containing 2 parts of sodium lauryl sulphate. The liquor ratio is 1:40. At 40°–50° 100 parts of a scoured fabric of polyester fibre are entered into the bath, and after the addition of 20 parts of an emulsion of chlorinated benzene in water the bath is raised slowly to 100° and the fabric dyed for 1 – 2 hours at 95°–100°. It is then removed, rinsed, soaped, rinsed again and dried. The level yellow dyeing has excellent fastness to light, cross dyeing, washing, water, sea water, perspiration, sublimation, gas fumes, pleating and permanent press finishing.

B. A mixture of 30 parts of the dye of Example 2, 40 parts of sodium dinaphthylmethane disulphonate, 50 parts of sodium cetylsulphate and 50 parts of anhydrous sodium sulphate is ground in a ball mill to give a fine powder. 4 Parts of the powder are suspended in 1000 parts of water at 40°–50°. 100 Parts of a scoured fabric of polyester fibre are entered into the bath, which is then raised slowly to 130°. The fabric is dyed for about 1 hour at this temperature under pressure, and on removal is rinsed, soaped, rinsed and dried. A yellow dyeing with the same fastness properties as that of Example A is obtained.

C. A mixture of 20 parts of the dye of Example 3, 55 parts of sulphite cellulose waste lye and 800 parts of water is ground in a ball mill until the size of the dye particles is less than 1 micron. The colloidal solution thus obtained is mixed with 25 parts of ethylene glycolmonobutylether and 400 parts of carboxymethyl cellulose. This printing paste is highly suitable for the Vigoureux printing of polyester slubbing. The slubbing is printed with two rollers giving a coverage of 78% and without intermediate drying is steamed at 120°. Yellow prints having good fastness properties are obtained.

D. A mixture of 7 parts of the dye of Example 3, 13 parts of sulphite cellulose waste lye and 100 parts of water is ground in a ball mill and the resulting paste is dried in an atomizer. 4 Parts of the dye preparation thus obtained are pasted with a little water and added through a sieve to a bath of 4000 parts of water containing 4 parts of N-oleyl-N'-hydroxyethyl-N'-(3'-sulpho-2'-hydroxypropyl)-ethylenediamine. At 20° 100 parts of a fabric of nylon 66 fibre are entered into the bath, which is then raised over 30 minutes to 100°. The fabric is dyed for 1 hour at this temperature and subsequently rinsed and dried. A level yellow dyeing is obtained which has good fastness to light, cross dyeing, washing, sea water, perspiration, sublimation, rubbing and solvents.

E. A fine aqueous suspension of 30 parts of the dye of Example 4, 70 parts of sodium dinaphthylmethane disulphonate and 3 parts of sodium alginate is made up to 1000 parts with water and well stirred. A polyester fabric is padded with this liquor at 20°, air dried at 60°–100° and treated for 1 minute in dry air at 230°. It is then rinsed, soaped, rinsed again and dried. A fast, level dyeing is obtained.

Fabrics of synthetic polyamide fibre can be dyed by the same method.

In the following Table comprising Examples 5 to 180 further dyes are listed which can be produced in accordance with the procedures of Examples 1 to 4. These dyes have the fastness properties mentioned in the foregoing and give dyeings of yellow shade on polyester fibres. They are of the formula

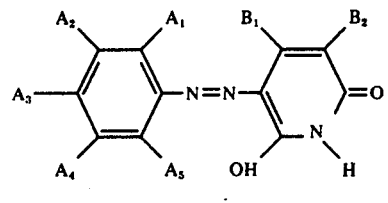

| Ex. No. | $A_1$ | $A_2$ | $A_3$ |
|---|---|---|---|
| 5 | —Cl | H | —$NO_2$ |
| 6 | H | H | " |
| 7 | —Br | H | " |
| 8 | —$SO_2CH_3$ | H | " |
| 9 | —$SO_2CH_2CH_3$ | H | " |
| 10 | —$NO_2$ | H | " |
| 11 | —CN | H | " |
| 12 | —$COOCH_3$ | H | " |
| 13 | —Cl | H | " |
| 14 | —$NO_2$ | H | " |
| 15 | —CN | H | —$NO_2$ |
| 16 | —$NO_2$ | H | —Cl |
| 17 | H | H | —$OCOCH_3$ |
| 18 | H | H | —CHO |
| 19 | —$NO_2$ | H | —$SO_2CH_3$ |
| 20 | —$CH_3$ | H | H |
| 21 | $C_2H_5OC_2H_4NHSO_2$— | H | H |
| 22 | H | —Cl | H |
| 23 | H | $\langle H \rangle$—NH—$SO_2$— | H |
| 24 | H | $C_6H_5$—$CH_2$—NH—$SO_2$— | H |
| 25 | —Cl | H | $C_6H_5$—NH—$SO_2$— |
| 26 | —$CH_3$ | H | $C_6H_5$—N($CH_3$)—$SO_2$— |
| 27 | H | H | Cl—$\langle \rangle$—NH—$SO_2$— |
| 28 | —Cl | Cl—$CH_2SO_2O$— | —Cl |
| 29 | H | H | CN—$C_2H_4SO_2O$— |
| 30 | $H_5C_2SO_2O$— | H | H |
| 31 | H | Cl | $H_5C_2OC_2H_4$—$SO_2O$— |
| 32 | $CH_3$ | $CH_3SO_2O$— | H |
| 33 | H | Cl | $(CH_3)_2CH$—$SO_2O$— |
| 34 | $CH_3$— | H | H |
| 35 | H | H | $NO_2$— |
| 36 | H | H | $H_5C_2O$— |
| 37 | —Cl | H | H |
| 38 | H | H | $F_3C$— |
| 39 | H | $H_2NSO_2$— | H |
| 40 | $H_2NSO_2$— | H | $H_3C$— |
| 41 | " | $H_3C$— | H |
| 42 | " | H | —$OCH_3$ |
| 43 | $H_5C_2NH$—$SO_2$— | H | H |
| 44 | —$CH_3$ | $H_3C$—NH—$SO_2$— | H |
| 45 | " | H | H |
| 46 | —Cl | $H_2N$—$SO_2$— | —Cl |
| 47 | —Cl | H | H |
| 48 | —Cl | H | H |
| 49 | —Cl | H | H |
| 50 | —Cl | H | $H_3C$—$SO_2$— |
| 51 | H | H | —$OCH_3$ |
| 52 | H | —$OCH_3$ | H |
| 53 | H | H | —$OCH_3$ |
| 54 | —$NO_2$ | H | " |
| 55 | " | H | $H_2NSO_2$— |
| 56 | —OH | H | $H_2NSO_2$— |
| 57 | H | —CN | H |
| 58 | H | —Cl | H |
| 59 | —$NO_2$ | H | H |
| 60 | —Cl | H | H |
| 61 | —CN | H | Cl |
| 62 | Cl | H | $H_3CSO_2$— |
| 63 | Cl | H | $(H_3C)_2NSO_2$— |
| 64 | Cl | H | " |
| 65 | H | H | $C_6H_5$—CO—NH— |
| 66 | H | H | $H_3C$—CO—NH— |
| 67 | H | H | $C_6H_5$—$CH_2OCO$— |
| 68 | H | H | $H_3CO$—$C_2H_4OCO$— |

-continued

| # | Col1 | Col2 | Col3 |
|---|---|---|---|
| 69 | $-OCH_3$ | H | $-NO_2$ |
| 70 | H | $NO_2$ | H |
| 71 | $-CH_3$ | H | $-OH$ |
| 72 | $-Cl$ | H | H |
| 73 | H | $C_6H_5-CH_2-SO_2O-$ | $C_6H_5-SO_2O-$ |
| 74 | H | $CH_3$ | |
| 75 | H | $CH_3$ | 4-Cl-$C_6H_4-SO_2O-$ |
| 76 | $OCH_3$ | H | 4-$H_3CO-C_6H_4-SO_2O-$ |
| 77 | $-NO_2$ | H | $-CH_3$ |
| 78 | $-CH_3$ | H | $-CH_3$ |
| 79 | H | $-Cl$ | Cl |
| 80 | H | $-Cl$ | Cl |
| 81 | H | H | piperidino-$SO_2-$ |
| 82 | H | H | $(HOC_2H_4)_2N-SO_2-$ |
| 83 | H | morpholino-$SO_2O-$ | H |
| 84 | H | $C_6H_5-N(CH_3)-SO_2O-$ | H |
| 85 | H | H | aziridino-$SO_2O-$ |
| 86 | $-NO_2$ | H | $-SO_2CH_3$ |
| 87 | H | H | $CH_3OCO-$ |
| 88 | $CH_3SO_2O-$ | H | H |
| 89 | $BrC_2H_4SO_2O-$ | H | H |
| 90 | $H_9C_4SO_2O-$ | H | $-CH_3$ |
| 91 | $H_5C_2SO_2O-$ | H | H |
| 92 | H | $H_3CSO_2O-$ | H |
| 93 | H | $H_5C_2SO_2O-$ | H |
| 94 | $H_5C_6SO_2O-$ | H | H |
| 95 | $NCC_2H_4SO_2O-$ | H | H |
| 96 | H | $H_9C_4SO_2O-$ | H |
| 97 | $H_5C_6CH_2SO_2O-$ | H | H |
| 98 | H | H | $H_3CSO_2O-$ |
| 99 | H | H | $H_5C_2O-C_2H_4SO_2O-$ |
| 100 | H | H | $n-C_3H_7SO_2O-$ |
| 101 | H | H | cyclohexyl-$SO_2O-$ |
| 102 | $-CH_3$ | H | $H_3CSO_2O-$ |
| 103 | H | $-OCH_3$ | '' |
| 104 | H | $H_7C_3SO_2O-$ | H |
| 105 | $-Cl$ | H | H |
| | 2-Cl-$C_6H_4-SO_2O-$ | | |
| 106 | $ClCH_2SO_2O-$ | $-CH_3$ | H |
| 107 | $CH_3CHClSO_2O-$ | tert.$H_9C_4SO_2O-$ | H |
| 108 | $-CH_3$ | $n-C_6H_{13}SO_2O-$ | H |
| 109 | H | cyclohexyl-$SO_2O-$ | H |
| 110 | $-Cl$ | | |
| 111 | H | $-CH_3$ | $C_6H_5-SO_2O-$ |
| 112 | H | $-CH_3$ | $C_6H_5-SO_2O-$ |
| 113 | H | | 4-Cl-$C_6H_4-SO_2O-$ |
| 114 | $-OCH_3$ | H | 4-$CH_3-C_6H_4-SO_2O-$ |
| 115 | H | $-Cl$ | 3-$H_3CO-C_6H_4-SO_2O-$ |
| 116 | $(CH_3)_2NSO_2O-$ | H | H |
| 117 | $(H_9C_4)_2NSO_2O-$ | H | H |
| 118 | $(CH_3)_2NSO_2O-$ | H | H |
| 119 | $H_2NSO_2O-$ | H | H |
| 120 | $H_7C_3NHSO_2O-$ | H | H |
| 121 | H | $(H_3C)_2NSO_2O-$ | H |
| 122 | H | $(H_9C_4)_2NSO_2O-$ | H |
| 123 | H | morpholino-$SO_2O-$ | H |

-continued

| # | Col1 | Col2 | Col3 |
|---|---|---|---|
| 124 | H | piperidine-N-SO$_2$O— | H |
| 125 | H | C$_6$H$_5$—NHSO$_2$O— | H |
| 126 | H | C$_6$H$_5$—N(CH$_3$)SO$_2$O— | H |
| 127 | H | —CH$_3$ | (CH$_3$)$_2$NSO$_2$O— |
| 128 | H | H | (H$_3$C)$_2$NSO$_2$O— |
| 129 | H | —CH$_3$ | (H$_3$C)$_2$NSO$_2$O— |
| 130 | H | C$_6$H$_5$—N(C$_2$H$_5$)SO$_2$O— | H |
| 131 | H | H | H$_3$CO—C$_6$H$_4$—NHSO$_2$O— |
| 132 | H$_3$C—C$_6$H$_4$—NHSO$_2$O— (4-methyl) | —CH$_3$ | H |
| 133 | H$_3$C—C$_6$H$_4$—NHSO$_2$O— (3-methyl) | H | —CH$_3$ |
| 134 | 2-CH$_3$-C$_6$H$_4$—NHSO$_2$O— | —CH$_3$ | " |
| 135 | Cl—C$_6$H$_4$—NHSO$_2$O— | H | —OCH$_3$ |
| 136 | C$_6$H$_5$—NHSO$_2$O— | H | H |
| 137 | H | H$_5$C$_6$CH$_2$NHSO$_2$O— | H |
| 138 | H | H$_5$C$_6$(C$_6$H$_{13}$)NSO$_2$O— | —CH$_3$ |
| 139 | —CH$_3$ | Cl—C$_2$H$_4$NHSO$_2$O— | H |
| 140 | H | H$_5$C$_2$OC$_2$H$_4$NH—SO$_2$O— | —CH$_3$ |
| 141 | —Cl | H$_7$C$_3$NHSO$_2$O— | —Cl |
| 142 | H | —CH$_3$ | H$_9$C$_4$NHSO$_2$O— |
| 143 | H | —CH$_3$ | (H$_7$C$_3$)$_2$NSO$_2$O— |
| 144 | H | H$_5$CO— | (H$_7$C$_3$)$_2$NSO$_2$O— |
| 145 | —OCH$_3$ | H | (iso-C$_4$H$_9$)$_2$NSO$_2$O— |
| 146 | H | —Cl | (H$_9$C$_4$)$_2$NSO$_2$O— |
| 147 | H | H | H$_7$C$_3$NHSO$_2$O— |
| 148 | H | H | H$_3$CCO—NH—C$_6$H$_4$—CH$_3$ (with NO$_2$) |
| 149 | H | H | O$_2$N—C$_6$H$_3$(CH$_3$)(NO$_2$)— |
| 150 | H | H | C$_6$H$_5$—NH—SO$_2$— |
| 151 | H | H | C$_6$H$_5$—N=N— |
| 152 | H | —OCH$_3$ | O$_2$N—C$_6$H$_4$—N=N— |
| 153 | H | H$_5$C$_6$(CH$_3$)NSO$_2$O— | H |
| 154 | H | (CH$_3$)$_2$NSO$_2$O— | H |
| 155 | H | aziridine-N-SO$_2$O— | H |
| 156 | —NO$_2$ | H | morpholine-N-SO$_2$O— |
| 157 | H | cyclohexyl-NHSO$_2$O— | H |
| 158 | H | NC—C$_2$H$_4$—SO$_2$O— | H |
| 159 | NC—C$_2$H$_4$—SO$_2$O— | H | H |
| 160 | morpholine-N—SO$_2$O— | H | —OCH$_3$ |
| 161 | —Cl | (CH$_3$)$_2$NSO$_2$O— | Cl |
| 162 | H | H | C$_6$H$_5$—SO$_2$O— |
| 163 | H | H | H$_3$CO—C$_6$H$_4$—SO$_2$O— |
| 164 | H | CH$_3$SO$_2$O— | Cl |
| 165 | H | " | —CH$_3$ |
| 166 | —CH$_3$ | H$_5$C$_6$CH$_2$SO$_2$O— | —CH$_3$ |
| 167 | —CH$_3$ | CH$_3$SO$_2$O— | H |
| 168 | CH$_3$SO$_2$O— | H | H$_3$C$_2$—O—C$_2$H$_4$SO$_2$O— |
| 169 | H | —Cl | H |
| 170 | H | CH$_3$SO$_2$— | H |
| 171 | H | (H$_3$C)$_2$NSO$_2$O— | |

-continued

| No. | A | A' | (structure) |
|---|---|---|---|
| 172 | H | H | 2,5-dichlorophenyl-N=N– |
| 173 | H | H | 3-cyanophenyl-N=N– |
| 174 | H | H | 4-methoxyphenyl-N=N– (H₃CO-C₆H₄-N=N–) |
| 175 | H | H | 2-methylphenyl-N=N– |
| 176 | H | H | 4-acetylphenyl-N=N– (H₃CCO-C₆H₄-N=N–) |
| 177 | H | H | 4-methylsulfonylphenyl-N=N– (H₃CSO₂-C₆H₄-N=N–) |
| 178 | H | H | 4-ethoxyphenyl-N=N– (C₂H₅O-C₆H₄-N=N–) |
| 179 | –NO₂ | H | H |
| 180 | Cl | H | H |

| Ex. No. | $A_1$ | $A_5$ | $B_1$ | $B_2$ |
|---|---|---|---|---|
| 5 | H | –CN | Phenyl | –CN |
| 6 | H | H |  | " |
| 7 | H | H | 3-pyridyl | " |
| 8 | H | H | thiazolyl | " |
| 9 | H | H | 2-thienyl | " |
| 10 | H | H | 4-methoxyphenyl (H₃CO-C₆H₄–) | " |
| 11 | H | H | 4-chloro-2-methylphenyl | " |
| 12 | H | H | 4-acetylphenyl (H₃CCO-C₆H₄–) | " |
| 13 | H | Cl | 2-cyanophenyl | –CO–C₆H₁₁ |
| 14 | H | –Br | 4-methylphenyl (CH₃–C₆H₄–) | –CN |
| 15 | H | –Br | 4-nitro-2-methylphenyl (O₂N-C₆H₃(CH₃)–) | –CN |
|  |  |  | 2-phenylbenzothiazolyl |  |
| 16 | H | H | –C₆H₅ | –COCH₃ |
| 17 | H | H | " | –CO–C₆H₅ |
| 18 | H | H | " | –SO₂–CH₃ |
| 19 | H | H | " | –SO₂–C₆H₅ |
| 20 | ClC₂H₄NHSO₂– | H | –C₆H₅ | –SO₂NH₂ |
| 21 | –Cl | H | " | –SO₂–N(CH₃)–C₆H₅ |
| 22 | morpholino-N–SO₂– | H | " | –SO₂–NH–C₃H₇ |
| 23 | CH₃– | H | " | –SO₂–N(CH₃)₂ |
| 24 | H | H | " | –CO–N(CH₃)–C₆H₅ |
| 25 | H | H | " | –COOC₂H₅ |
| 26 | H | H | " | –CONH₂ |
| 27 | H | H | " | –CONHC₆H₅ |
| 28 | H | H | " | –CON(CH₃)C₃H₇ |
| 29 | H | H | –C₆H₅ | –COOCH₃ |

| | | | | |
|---|---|---|---|---|
| 30 | —OCH₃ | H | " | —COO—C₆H₅ |
| 31 | Cl | H | " | 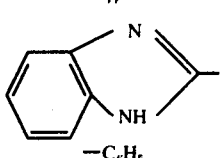 |
| 32 | —CH₃ | H | " | —CN |
| 33 | H | H | 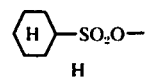 | " |
| 34 | 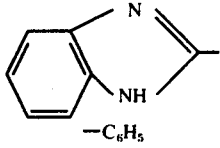 | H | " | 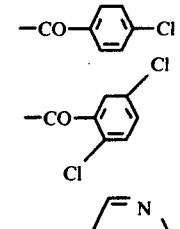 |
| 35 | H | H | " | 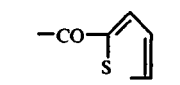 |
| 36 | H | H | " | 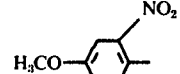 |
| 37 | Cl | H | " | 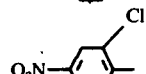 |
| 38 | H | H |  | —SO₂CH₃ |
| 39 | H | H | 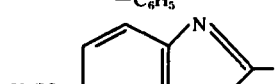 | —COCH₃ |
| 40 | H | H | —C₆H₅ | —CO—CH₂—C₆H₅ |
| 41 | H₃C— | H |  | —CN |
| 42 | H | H | 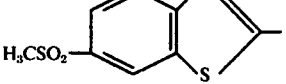 | " |
| 43 | Cl | H | 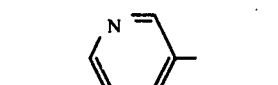 | —COCH₃ |
| 44 | H | H | 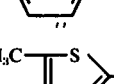 | —CO—C₆H₅ |
| 45 | H₃C—NH—SO₂— | H | | —CN |
| 46 | H | H |  | " |
| 47 | NC—C₂H₄—SO₂— | H | 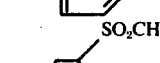 | " |
| 48 | Cl—C₂H₄—SO₂— | H |  | " |
| 49 | CH₃—O—C₂H₄—SO₂— | H | 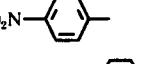 | " |
| 50 | H | —NO₂ | 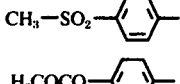 | —CN |
| 51 | H | H | 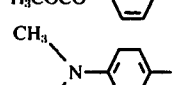 | " |
| 52 | H | H | 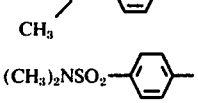 | " |

-continued

| No. | | | | |
|---|---|---|---|---|
| 53 | H | H | CH₃—OC₂H₄—OCO—C₆H₄— | " |
| 54 | H | H | H₅C₂OOC—C₆H₄— | " |
| 55 | H | H | 2-OC₂H₅, 5-OC₂H₅-C₆H₃— | " |
| 56 | H | H | 1-naphthyl | " |
| 57 | H | H | 2-naphthyl | " |
| 58 | H | H | " | " |
| 59 | H | H | 6-H₃C-2-naphthyl | " |
| 60 | H | H | 6-O₂N-2-naphthyl | " |
| 61 | H | H | 4-H₃CO-1-naphthyl | —CN |
| 62 | H | H | —C₆H₅ | " |
| 63 | Cl | H | " | " |
| 64 | H | Cl | " | " |
| 65 | H | H | H₃CO—C₆H₄— | " |
| 66 | H | H | Cl—C₆H₄— | " |
| 67 | H | H | —C₆H₅ | —COCH₃ |
| 68 | H | H | " | —CN |
| 69 | H | H | 2,4-Cl₂—C₆H₃— | " |
| 70 | H | H | —C₆H₅ | " |
| 71 | H | H | 2,4-(CH₃)₂—C₆H₃— | " |
| 72 | —SO₂CH₃ | H | —C₆H₅ | " |
| 73 | H₃C— | H | H₃CO—C₆H₄— | —CN |
| 74 | H | H | —C₆H₅ | " |
| 75 | H | H | " | " |
| 76 | H | H | HO—C₆H₄— | " |
| 77 | H | H | CH₃—OCO—C₆H₄— | " |
| 78 | H | NO₂ | C₂H₅OOC—C₆H₄— | " |
| 79 | H | H | —C₆H₅ | " |
| 80 | Cl | H | " | " |
| 81 | H | H | H₃CO—C₂H₄—O—C₆H₄— | " |
| 82 | H | H | —C₆H₅ | " |
| 83 | H | H | " | —COCH₃ |
| 84 | H | H | " | " |
| 85 | H | H | " | —CN |
| 86 | H | H | —C₆H₅ | —CN |
| 87 | H | H | 2,4-Cl₂—C₆H₃— | " |
| 88 | H | H | 4-CH₃—C₆H₄— | —SO₂CH₃ |

-continued

| | | | | |
|---|---|---|---|---|
| 89 | H | H | 3,5-(H₃C)₂-C₆H₃- | —CN |
| 90 | H | H | 2-CH₃-C₆H₄- | " |
| 91 | —CH₃ | H | 2,4-(H₃C)₂-C₆H₃- | —SO₂NHC₃H₇ |
| 92 | H | H | 2,4,5-(CH₃)₃-C₆H₂- | —CN |
| 93 | H | —CH₃ | 2,4,5-(CH₃)₃-C₆H₂- | " |
| 94 | H | H | 2,4,6-(CH₃)₃-C₆H₂- | —SO₂—C₆H₅ |
| 95 | H | H | 4-H₅C₂-C₆H₄- | —CN |
| 96 | H | H | 4-(H₃C)₂CH-C₆H₄- | —SO₂C₂H₅ |
| 97 | H | H | 4-H₉C₄-C₆H₄- | —SO₂NH₂ |
| 98 | H | H | 4-H₃CO-C₆H₄- | —CO—CH₂—C₆H₅ |
| 99 | H | H | 3-H₃CO-C₆H₄- | —CN |
| 100 | H | H | 2-OCH₃-C₆H₄- | —SO₂N(CH₃)—C₆H₅ |
| 101 | H | H | 4-Br-C₆H₄- | —COCH₃ |
| 102 | H | —CH₃ | 2,4-Cl₂-C₆H₃- | —COOCH₂—C₆H₅ |
| 103 | H | H | 4-NCS-C₆H₄- | —CN |
| 104 | H | H | 4-O₂N-C₆H₄- | —COC₃H₇ |
| 105 | H | H | 4-O₂N-2-OCH₃-C₆H₃- | —SO₂N(CH₃)₂ |
| 106 | H | H | 4-NC-C₆H₄- | —CN |
| 107 | H | H | 4-(C₂H₅—CO—NH)-C₆H₄- | —CO—C₆H₄—Cl |
| 108 | H | H | 4-(CH₃CO—NH)-C₆H₄- | —CO-thienyl |
| 109 | H | H | 4-H₃CCO-C₆H₄- | —CN |
| 110 | H | —Cl | 4-(CH₃)₂N-C₆H₄- | —CO-pyridyl |
| 111 | H | H | 4-H₉C₄NH-C₆H₄- | —CN |

-continued

| No. | | | | |
|---|---|---|---|---|
| 112 | —CH₃ | H | (H₃C)₂NSO₂—C₆H₄— | —COCH₃ |
| 113 | H | H | H₅C₂NH—SO₂—C₆H₄— | —CN |
| 114 | H | H | —C₆H₅ | " |
| 115 | H | H | —C₆H₅ | —CN |
| 116 | H | H | " | " |
| 117 | H | H | " | " |
| 118 | —Cl | H | H₅C₂OOC—C₆H₄— | " |
| 119 | H | H | (H₃C)₂NCO—C₆H₄— | " |
| 120 | H | H | HO—C₆H₄— | —CN |
| 121 | H | H | HO-naphthyl | " |
| 122 | H | H | CH₃, OH-naphthyl | " |
| 123 | H | H | Cl—C₆H₄— | —SO₂CH₃ |
| 124 | H | H | Cl,Cl—C₆H₃— | —COCH₃ |
| 125 | H | H | furyl | " |
| 126 | H | H | thienyl | " |
| 127 | —CH₃ | H | H₃CO-thienyl | " |
| 128 | H | H | CH₃-thienyl | —SO₂CH₃ |
| 129 | H | H | H₃CSO₂-benzothiazolyl | —CN |
| 130 | H | H | Cl-benzimidazolyl | " |
| 131 | H | H | —C₆H₅ | " |
| 132 | H | H | Cl—C₆H₄— | " |
| 133 | —CH₃ | H | pyridyl | " |
| 134 | H | H | —C₆H₅ | " |
| 135 | H | H | " | " |
| 136 | —Cl | H | " | " |
| 137 | —CH₃ | H | H₃COCO—C₆H₄— | —CN |
| 138 | H | H | H₅C₂OOC—C₆H₄— | —CN |

| 139 | —CH₃ | H | H₃CO—⟨⟩— | " |
| 140 | H | H | —C₆H₅ | —CN |
| 141 | H | H | " | " |
| 142 | H | H | naphthyl | " |
| 143 | H | H | benzothiazolyl | " |
| 144 | H | H | thiazolyl | " |
| 145 | H | H | pyridyl | " |
| 146 | H | H | pyrrolyl | " |
| 147 | H | H | methylnaphthyl | " |
| 148 | H | H | —C₆H₅ | —CN |
| 149 | H | H | " | " |
| 150 | H | H | " | " |
| 151 | H | H | " | " |
| 152 | H | H | " | " |
| 153 | H | H | —C₆H₅ | —CN |
| 154 | H | H | " | " |
| 155 | H | H | " | " |
| 156 | H | H | " | " |
| 157 | H | H | " | " |
| 158 | H | H | " | " |
| 159 | Cl | H | " | " |
| 160 | H | H | —C₆H₅ | —CN |
| 161 | H | H | " | " |
| 162 | H | H | " | " |
| 163 | H | H | " | " |
| 164 | H | H | " | " |
| 165 | H | H | " | " |
| 166 | H | H | " | " |
| 167 | H | H | " | " |
| 168 | —CH₃ | H | " | " |
| 169 | H | H | " | " |
| 170 | H | H | benzothienyl | " |
| 171 | H | H | —C₆H₅ | " |
| 172 | H | H | " | " |
| 173 | H | H | —C₆H₅ | —CN |
| 174 | H | H | " | " |
| 175 | H | H | " | " |
| 176 | H | H | " | " |
| 177 | H | H | " | " |
| 178 | H | H | " | " |
| 179 | H | H | " | " |
| 180 | —CF₃ | H | " | " |

The dyes in the following table correspond to formula I.

| Exmpl. No. | R₁ | R₂ | R₃ |
|---|---|---|---|
| 181 |  | —CN | —C₆H₅ |

| Exmpl. No. | R₁ | R₂ | R₃ |
|---|---|---|---|
| 182 | ![structure: PhNH-SO₂-C₆H₄-NH-C₆H₃(NO₂)-] | " | " |
| 183 | ![structure: 2,4-dinitrophenyl-NH-C₆H₄-] | " | " |
| 184 | CH₃COHN-C₆H₄-C₆H₄- | " | CH₃-C₆H₄- |
| 185 | CH₃NHSO₂-naphthyl- | " | 2-thienyl |
| 186 | 1-ethoxy-naphth-2-yl | " | thiazolyl |
| 187 | PhNH-SO₂-C₆H₄-NH-C₆H₄(NO₂)- | " | —C₆H₅ |
Representative dyestuffs of the foregoing examples are as follows:
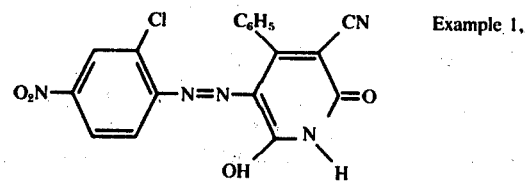
Example 1.
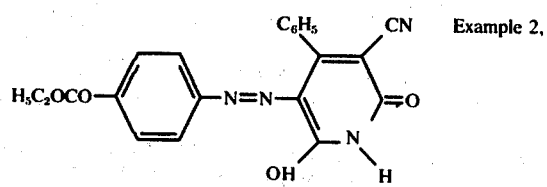
Example 2.
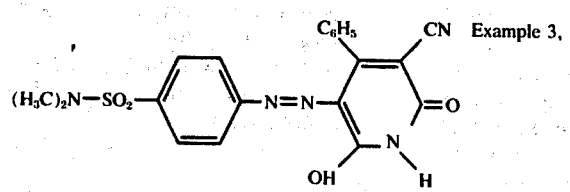
Example 3.

-continued

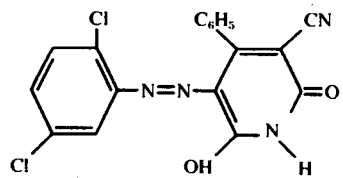

Example 4 a,

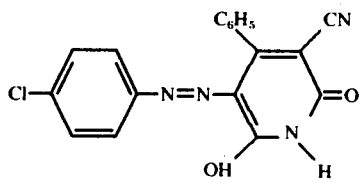

Example 4 b,

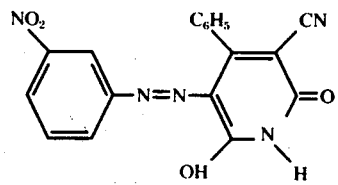

Example 70 and

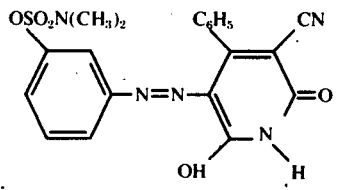

Example 171.

What is claimed is:
1. A compound of the formula

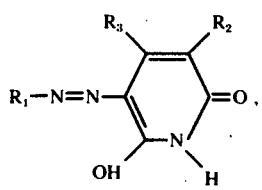

wherein

R₁ is phenyl, substituted phenyl, naphthyl or substituted naphthyl, wherein each substituent of substituted phenyl and substituted naphthyl is independently chloro, bromo, hydroxy, cyano, nitro, trifluoromethyl, alkyl, substituted alkyl, alkoxy, substituted alkoxy, acyl, acyloxy, acylamino, formyl, morpholinosulfonyl, piperidinosulfonyl, morpholinosulfonyloxy, aziridinoslfonyloxy, peripidinoslfonyloxy, alkylsulfamoylamilino, phenylsulfamoylanilino, dinitroanilino, alkylcarbonylaminophenyl, dinitrophenyl, phenylazo, nitrophenylazo, dichlorophenylazo, bromophenylazo, cyanophenylazo, methoxyphenylazo, ethoxyphenylazo, tolylazo or acylphenylazo, wherein each substituent of substituted alkyl and substituted alkoxy is independently chloro, bromo, alkoxy, phenyl, cyano, hydroxy or acyloxy, R₂ is cyano, acyl, thienylcarbonyl or pyridylcarbonyl, and R₃ is phenyl, naphthyl, thiazolyl, benzothiazolyl, thienyl, pyrrolyl, furyl, pyridyl, imidazolyl or benzimidazolyl, or a substituted derivative thereof, wherein each substituent is independently chloro, bromo, alkyl, substituted alkyl, alkoxy, substituted alkoxy, hydroxy, trifluoromethyl, cyano, thiocyano, nitro, alkylamino, dialkylamino, acyl, acyloxy or acylamino, wherein each substituent of substituted alkyl and substituted alkoxy is independently chloro, bromo, alkoxy, phenyl, cyano, hydroxy or acyloxy, wherein each acyl and acyl radical of each acyloxy, acylamino and acylphenylazo is independently R—X— or R'—Y', wherein R is lower alkyl, substituted lower alkyl, cyclohexyl, phenyl or substituted phenyl, wherein each substituent of substituted lower alkyl is independently chloro, bromo, alkoxy, phenyl, cyano, hydroxy or acyloxy, and each substituent of substituted phenyl is independently chloro, bromo, hydroxy, cyano, nitro, trifluoromethyl, alkyl or alkoxy, X is —CO—, —O—CO— or —SO₂—, R' is hydrogen or R, and Y is —NR'—CO— or —NR'—SO₂—, and each alkyl, alkoxy and alkyl and alkoxy radical of each substituted alkyl, substituted alkoxy, alkylsulfamoylanilino, alkylcarbonylaminophenyl, alkylamino and dialkylamino independently has 1 to 10 carbon atoms.

2. A compound according to claim 1 wherein R₁ is substituted phenyl, wherein each substituent of substituted phenyl is independently chloro, bromo, hydroxy, cyano, nitro, trifluoromethyl, lower alkyl, lower alkoxy, acyl, acyloxy, morpholinosulfonyl, piperidinosulfonyl, morpholinosulfonyloxy, aziridinosulfonyloxy, piperidinosulfonyloxy, benzamido, acetamido, 4-phenylsulfamoylanilino, 2,4-dinitroanilino, 4-acetamidophenyl, 2,4-dinitrophenyl, phenylazo, 4-nitrophenylazo, 2,5-dichlorophenylazo, 3-cyanophenylazo, 4-methoxyphenylazo, 4-ethoxyphenylazo, o-tolylazo, 4-acetylphenylazo or 4- methylsulfonylphenylazo, with the proviso that the phenyl ring of substituted phenyl has 1 to 3 substituents, $R_2$ is cyano or acyl, and $R_3$ is phenyl, naphthyl, 2-thiazolyl, 5-thiazolyl, 2-benzothiazolyl, 2-thienyl, 3-pyrrolyl, 2-furyl, 3-pyridyl or 2-benzimidazolyl, or a substituted derivative thereof, wherein each substituent is independently chloro, bromo, lower alkyl, lower alkoxy, hydroxy, cyano, thiocyano, nitro, lower alkylmino, dilower alkylamino, acyl, acyloxy or lower alkylcarbonylamino, with the proviso that each substituted derivative has 1 to 3 substituents, wherein each acyl and acyl radical of each acyloxy is independently R—X— or R'—Y—, wherein R is lower alkyl, monosubstituted lower alkyl, cyclohexyl, phenyl or monosubstituted phenyl, wherein the substituent of monosubstituted lower alkyl is chloro, bromo, lower alkoxy, phenyl, cyano or hydroxy, and the substituent of monosubstituted phenyl is chloro, lower alkyl or lower alkoxy, X is —CO—, —O—CO— or —SO$_2$—, R' is hydrogen or R, and Y is —NR'—CO— or NR'—SO$_2$—.

3. A compound according to claim 1 wherein
$R_1$ is phenyl or substituted phenyl,
$R_2$ is cyano or acyl, and
$R_3$ is phenyl or substituted phenyl, with the proviso that each substituted phenyl independently has 1 to 3 substituents.

4. A compound according to claim 3
wherein $R_2$ is cyano, and
$R_3$ is phenyl.

5. A compound according to claim 4
wherein $R_1$ is substituted phenyl, and each substituent of substituted phenyl independently is chloro, cyano, nitro, lower alkyl, lower alkoxy, acyl, acyloxy, morpholinosulfonyloxy, aziridinosulfonyloxy, phenylsulfamoylanilino, dinitroanilino, lower alkylcarbonylaminophenyl, dinitrophenyl, phenylazo, nitrophenylazo, dichlorophenylazo, cyanophenylazo, methoxyphenylazo, ethoxyphenylazo, tolylazo, acetylphenylazo or methylsulfonylphenylazo, wherein each acyl and acyl radical of acyloxy is independently R—X— or R'—Y—, wherein R is lower alkyl, monosubstituted lower alkyl, phenyl or monosubstituted phenyl, wherein the substituent of monosubstituted lower alkyl is lower alkoxy, cyano or phenyl, and the substituent of monosubstituted phenyl is chloro, lower alkyl or lower alkoxy, X is —SO$_2$— or —O—CO—, R' is hydrogen, lower alkyl, monosubstituted lower alkyl, cyclohexyl, phenyl or monosubstituted phenyl, wherein the substituent of monosubstituted lower alkyl is hydroxy or lower alkoxy and the substituent of monosubstituted phenyl is lower alkyl, lower alkoxy or chloro, and Y is —NR'—SO$_2$—.

6. A compound according to claim 5
wherein $R_1$ is substituted phenyl, and each substituent of substituted phenyl independently is chloro, nitro, cyano, methyl, methoxy, ethoxycarbonyl, 2-methoxyethoxycarbonyl, methylsulfonyl, methylsulfonyloxy, 2-ethoxyethylsulfonyloxy, 2-cyanoethylsulfonyloxy, benzylsulfonyloxy, phenylsulfonyloxy, 4-chlorophenylsulfonyloxy, p-tolylsulfonyloxy, 3-methoxyphenylsulfonyloxy, 4-methoxyphenylsulfonyloxy, dimethylsulfamoyl, di(2-hydroxyethyl)sulfamoyl, phenylsulfamoyl, propylsulfamoyloxy, dimethylsulfamoyloxy, dibutylsulfamoyloxy, cyclohexylsulfamoyloxy, 2-ethoxyethylsulfamoyloxy, phenylsulfamoyloxy, N-methyl-N-phenylsulfamoyloxy, o-tolylsulfamoyloxy, 4-methoxyphenylsulfamoyloxy, 4-chlorophenylsulfamoyloxy, morpholinosulfonyloxy, aziridinosulfonyloxy, 4-phenylsulfamoylanilino, 2,4-dinitroanilino, 4-actamidophenyl, 2,5-dichlorophenylazo, 3-cyanophenylazo, 4-methoxyphenylazo, 4-ethoxyphenylazo, o-tolylazo, 4-acetylphenylazo or 4-methylsulfonylphenylazo.

7. A compound according to claim 5 wherein X is —SO$_2$—.

8. The compound according to claim 6 of the formula

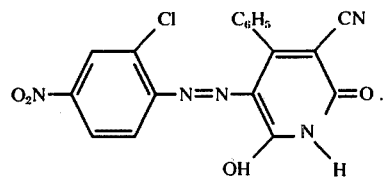

9. The compound according to claim 6 of the formula

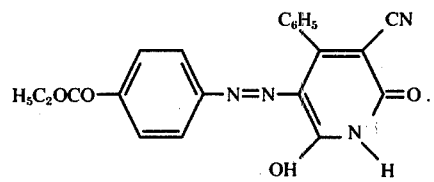

10. The compound according to claim 6 of the formula

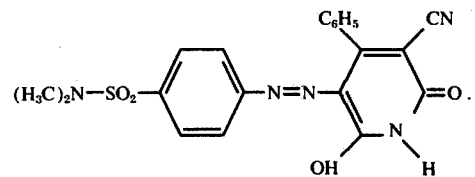

11. The compound according to claim 6 of the formula

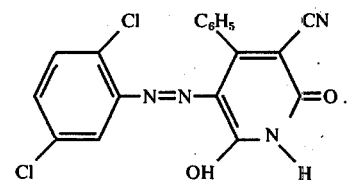

12. The compound according to claim 6 of the formula

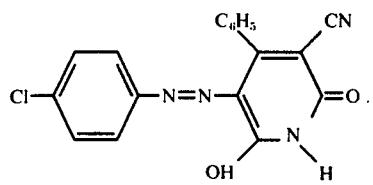
13. The compound according to claim 6 of the formula
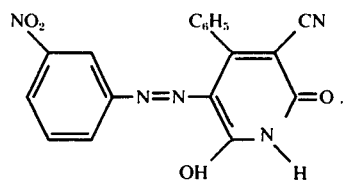
14. The compound according to claim of the formula
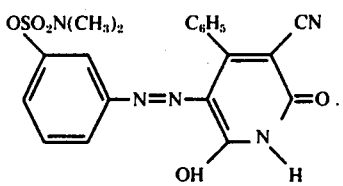
15. The compound according to claim 6 of the formula
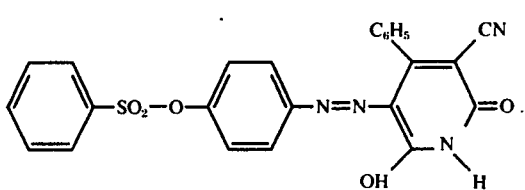
* * * * *